United States Patent [19]

Narula et al.

[11] Patent Number: 5,039,659

[45] Date of Patent: Aug. 13, 1991

[54] 2,2,3-TRIMETHYLCYCLOPENTENYL ACETONE DERIVATIVES, ORGANOLEPTIC USES THEREOF AND PROCESS FOR PREPARING SAME

[75] Inventors: Anubhav P. S. Narula, Hazlet; John J. De Virgilio, Freehold, both of N.J.; Vincent F. Kuczinski, Staten Island, N.Y.; Anton V. Ouwerkerk, Livingston, N.J.; Charles E. J. Beck, Summit, N.J.; Kathleen E. Boardwick, Keyport, N.J.; Marie R. Hanna, Keyport, N.J.

[73] Assignee: International Flavors & Fragrances Inc., New York, N.Y.

[21] Appl. No.: 563,607

[22] Filed: Aug. 7, 1990

[51] Int. Cl.$^5$ ............................................. A61K 7/46
[52] U.S. Cl. ................................. 512/8; 512/16; 512/18; 512/26; 512/27; 568/377
[58] Field of Search ............... 568/377; 512/8, 18, 512/26, 27, 16

[56] References Cited

U.S. PATENT DOCUMENTS

| 4,208,296 | 6/1980 | Yoshida et al. | 512/8 |
| 4,619,781 | 10/1986 | Wieger et al. | 512/8 |
| 4,652,402 | 3/1987 | Brunke et al. | 512/8 |
| 4,666,629 | 0/1987 | Wieger et al. | 512/8 |

FOREIGN PATENT DOCUMENTS 0139330  10/1980  Japan .............................. 512/8

OTHER PUBLICATIONS

Wawrzencyk et al., "Chem. Abstracts", vol. 96; 122285z (1981).
Derdzinski, "Chemical Abstracts", vol. 96:122286a (1981).
Wawrzenczyk et al., (II)-Juvenoids with Cyclopentene Ring. Synthesis of Isopropyl 3,7-Dimethyl-10-(2,2,3--trimethylcyclopent-3-en-l-yl)-deca-2,8-dienoate and -deca-2,4,8-trienoate, Journal F. Pfraft. Chemie. Band 326, Heft 2, 1984, S. 213–221.

Primary Examiner—Werren B. Lone

Attorney, Agent, or Firm—Arthur L. Liberman

[57] ABSTRACT

Described are 2,2,3-trimethylcyclopentenyl acetone derivatives defined according to one or a mixture of compounds having the structures:

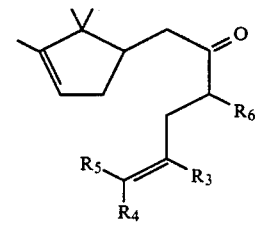

and

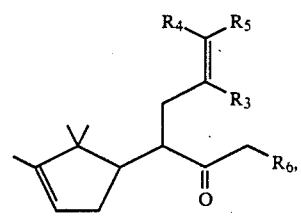

organoleptic uses thereof, processes for preparing same using as a starting material the compound having the structure:

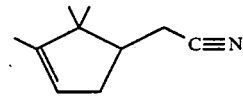

which is reacted to form the compound having the structure:

(Abstract continued on next page.)

GLC PROFILE FOR EXAMPLE II

5,039,659
Page 2

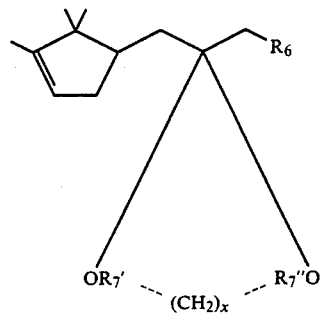

which is then converted to the 2,2,3-trimethylcyclopentenyl acetone derivatives or our invention using the allylic alcohol having the structure:

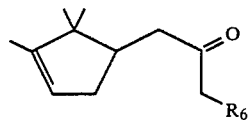

which is further reacted to form the novel intermediate:

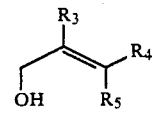

wherein $R_3$, $R_4$, and $R_5$ are the same or different hydrogen or methyl; $R_6$ represents hydrogen, methyl, ethyl, or propyl or isopropyl; x is 0, 1 or 2; $R_7$ is methyl or ethyl; $R_7'$ and $R_7''$ represent methyl or ethyl or $R_7'$, $(CH_2)_x$ and $R_7''$ taken together represents $C_2$–$C_6$ alkylene; M represents Li, Mg, X or MgX; and X represents chloro or bromo.

12 Claims, 9 Drawing Sheets

GLC PROFILE FOR EXAMPLE II.

GLC PROFILE FOR EXAMPLE III.

NMR SPECTRUM FOR EXAMPLE III, PEAK 21 OF Fig. 2

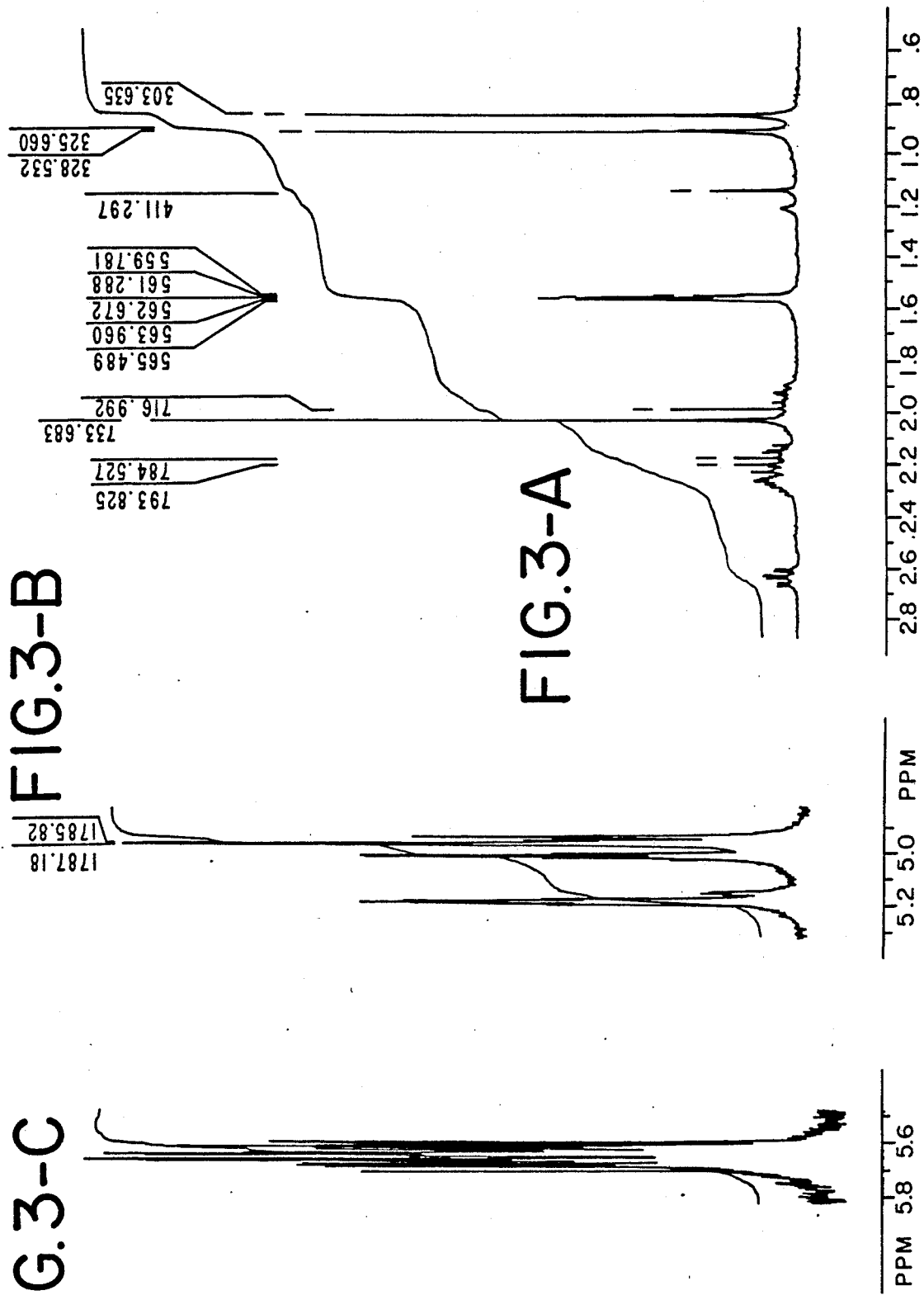

NMR SPECTRUM FOR EXAMPLE III, PEAK 22 OF FIG. 2.

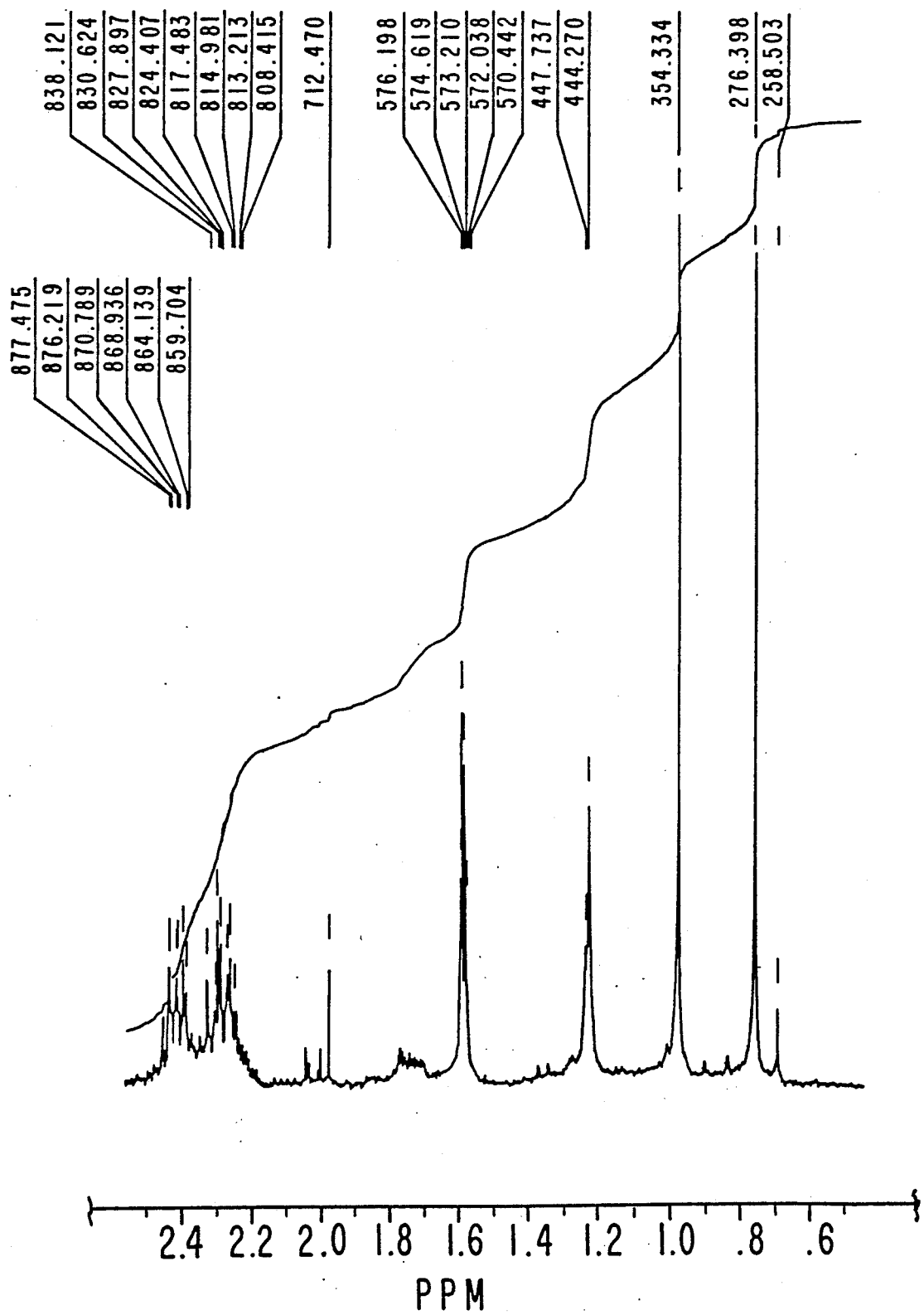

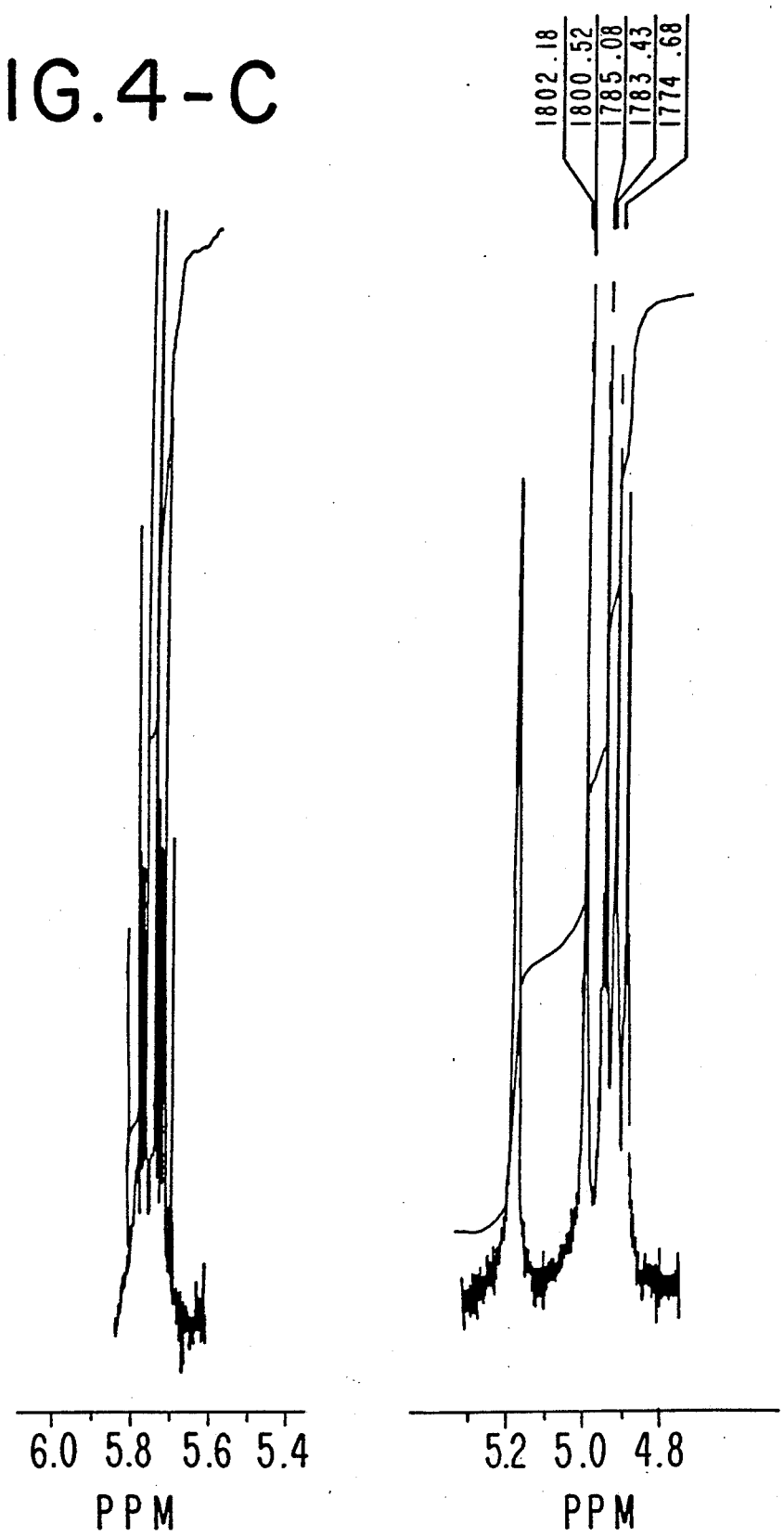

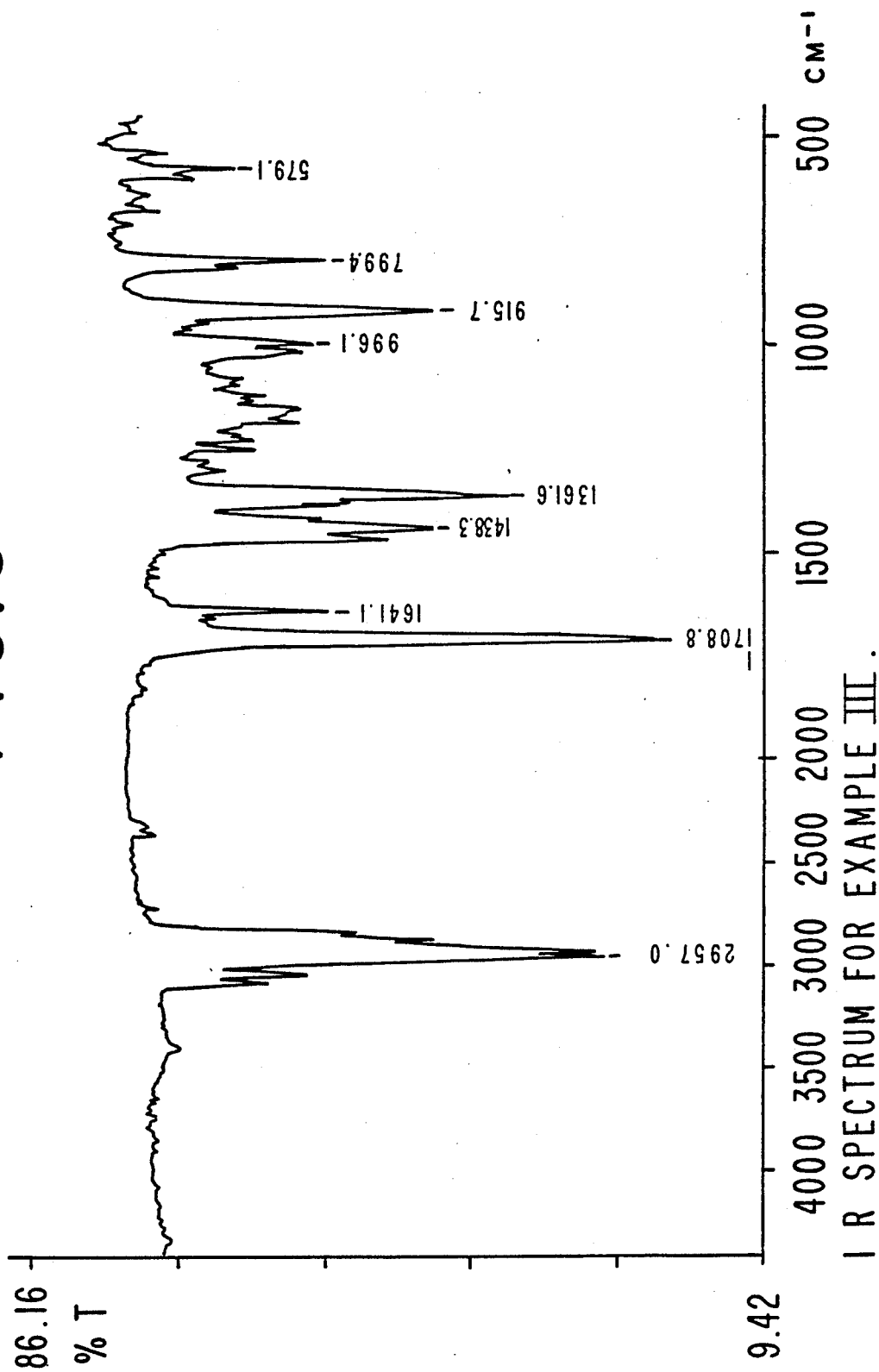

2,2,3-TRIMETHYLCYCLOPENTENYL ACETONE DERIVATIVES, ORGANOLEPTIC USES THEREOF AND PROCESS FOR PREPARING SAME

BACKGROUND OF THE INVENTION

Described are 2,2,3-trimethylcyclopentenyl acetone derivatives defined according to at least one of the structures:

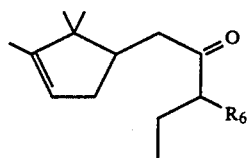

and

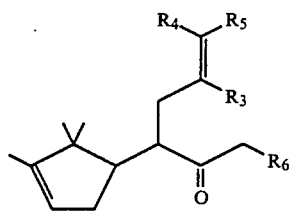

as well as processes for making the same, intermediates used in such processes defined according to the structure:

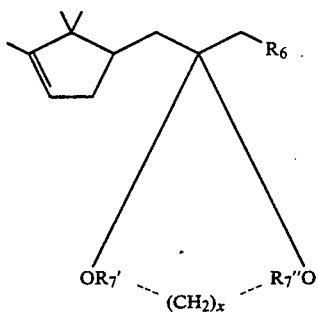

and organoleptic uses thereof, particularly uses thereof in augmenting or enhancing the aroma of perfume compositions colognes and perfumed articles.

(Wherein $R_3$, $R_4$, and $R_5$ are the same or different hydrogen or methyl; $R_6$ represents hydrogen, methyl, ethyl, propyl or isopropyl; x is 0, 1 or 2; $R_7'$ and $R_7''$ represent methyl or ethyl or $R_7,(CH_2)_x$ and $R_7''$ taken together represents $C_2$-$C_6$ alkylene).

Inexpensive, long lasting and intense sweet, green, fruity, pineapple, galbanum and geranium profiles with sweet, fruity, pineapple and green topnotes are highly desirable in the art of perfumery. Many of the natural materials which provide such fragrances and contribute such desired nuances to perfumery compositions as well as perfumed articles including solid or liquid anionic, cationic, nonionic or zwitterionic detergents, perfumed polymers, fabric softener compositions, fabric softener articles, hair preparations, cosmetic powders and the like are high in cost, vary in quality from one batch to another and/or are generally subject to the usual variations of natural products.

Trimethyl substituted cyclopentene acetone derivatives and their alcohol derivatives are known in the art of perfumery. In addition, trimethyl substituted cyclopentene acetone derivatives are known for other uses.

Thus, the compound having the structure:

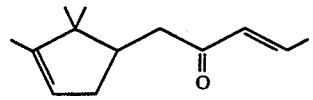

is described by Wawrzenczyk, et al. in Chem. Abstracts Vol. 96, No. 122285 (Abstract of Polish Patent 110257) as having a "fruity odor". Dardzynski, et al. describes the compound having the structure:

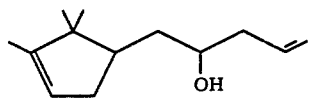

as having a flowery odor at Chem. Abstracts Vol. 96, No. 122286a (Abstract of Polish Patent 110254). Furthermore, Wawrzenczyk, et al. describes the synthesis of the compound having the structure:

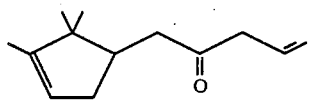

at Chem. Abstracts Vol. 101:72956t (Abstract of J. Parkt. Chem. 1984, 326(2), 213-21)

Synthesis of allylic substituted ketone derivatives for the purpose of producing perfumery derivatives is also known as is set forth in Sprecker, et al. U.S. Pat. No. 4,933,320 issued on June 12, 1990 wherein the reaction scheme to wit:

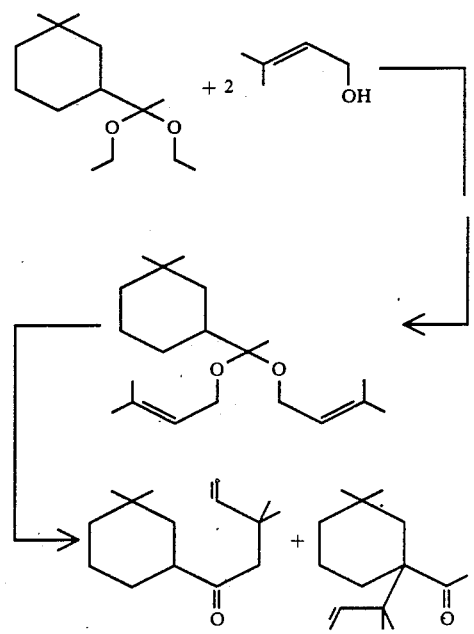

is set forth.

Nothing in the prior art, however, describes the 2,2,3-trimethylcyclopentenyl acetone derivatives or infers their organoleptic uses which are unexpected, unobvious and advantageous.

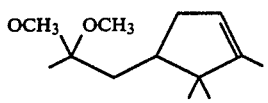

Figure 2:
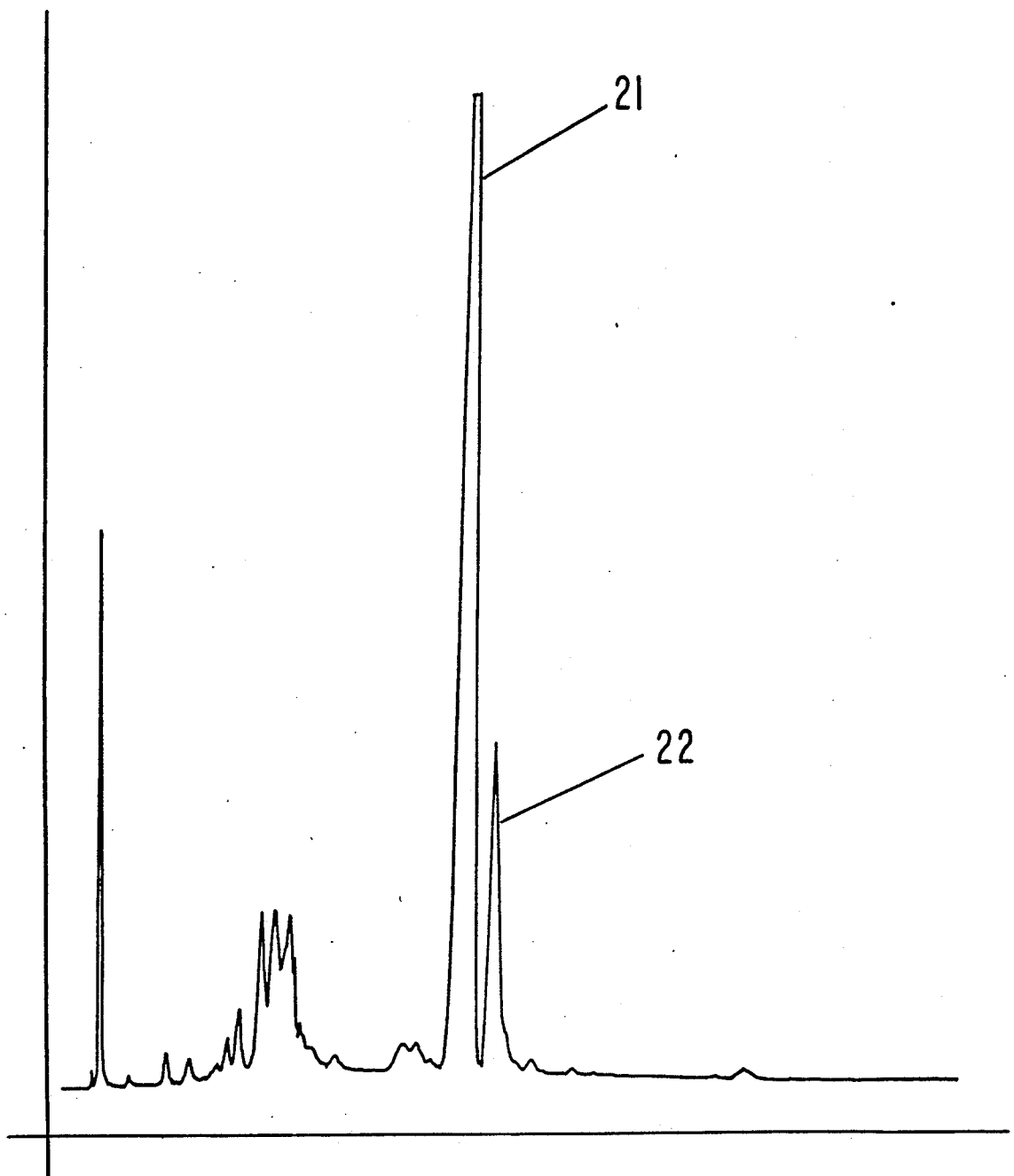

FIG. 2 is the GLC profile for the reaction product of Example III containing the compounds having the structures:

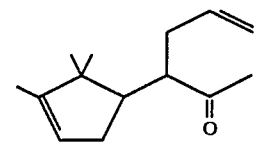

and

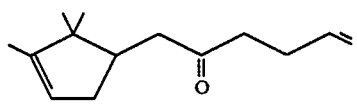

Figure 3:
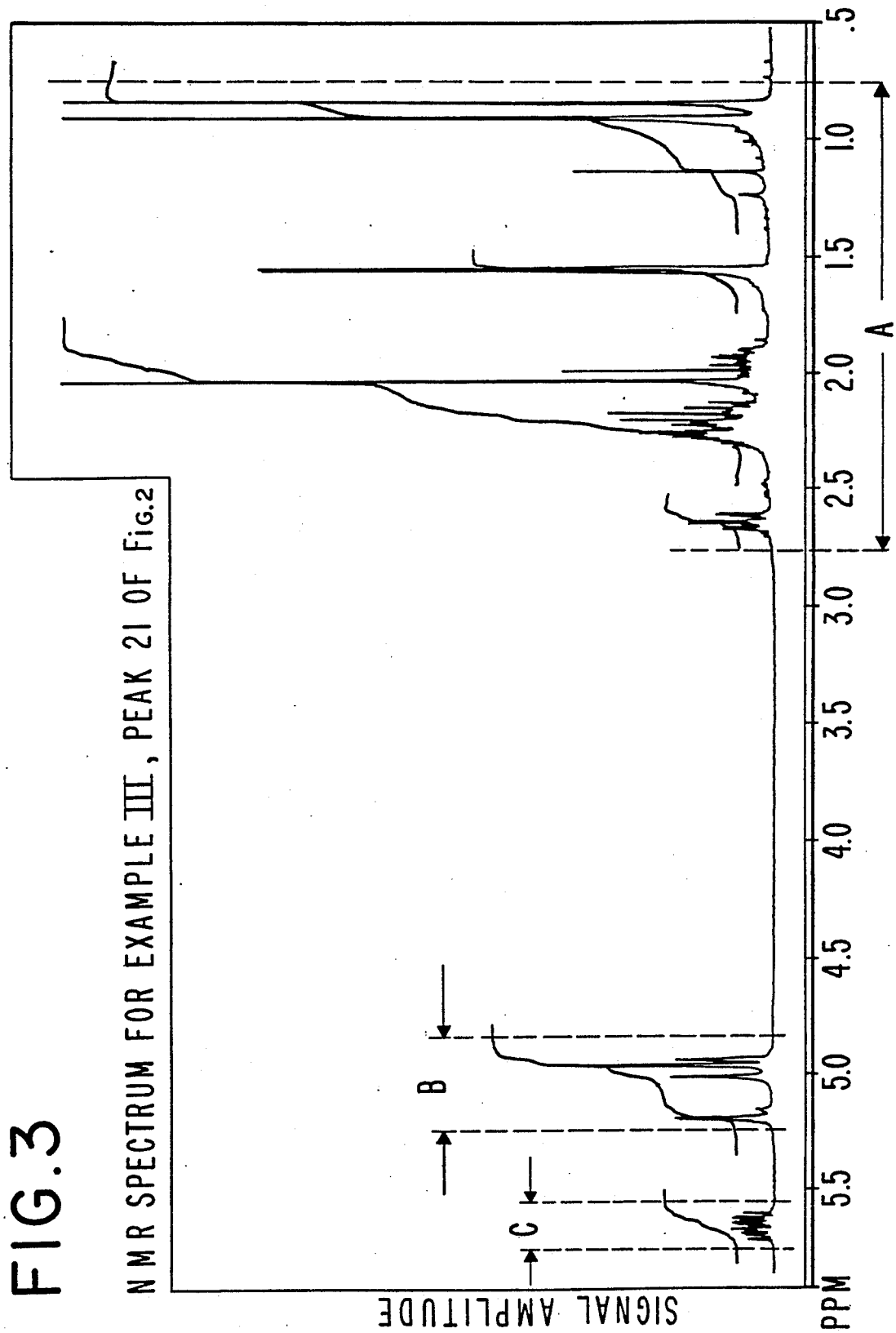

FIG. 3 is the NMR spectrum for the peak indicated by reference numeral 21 of FIG. 2 for the compound having the structure:

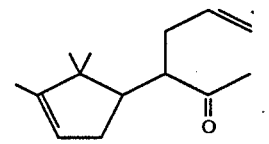

prepared according to Example III.

FIGS. 3A, 3B and 3C represent details of enlarged sections of the NMR spectrum of FIG. 3 denoted on FIG. III as sections "A", "B", and "C".

Figure 4:
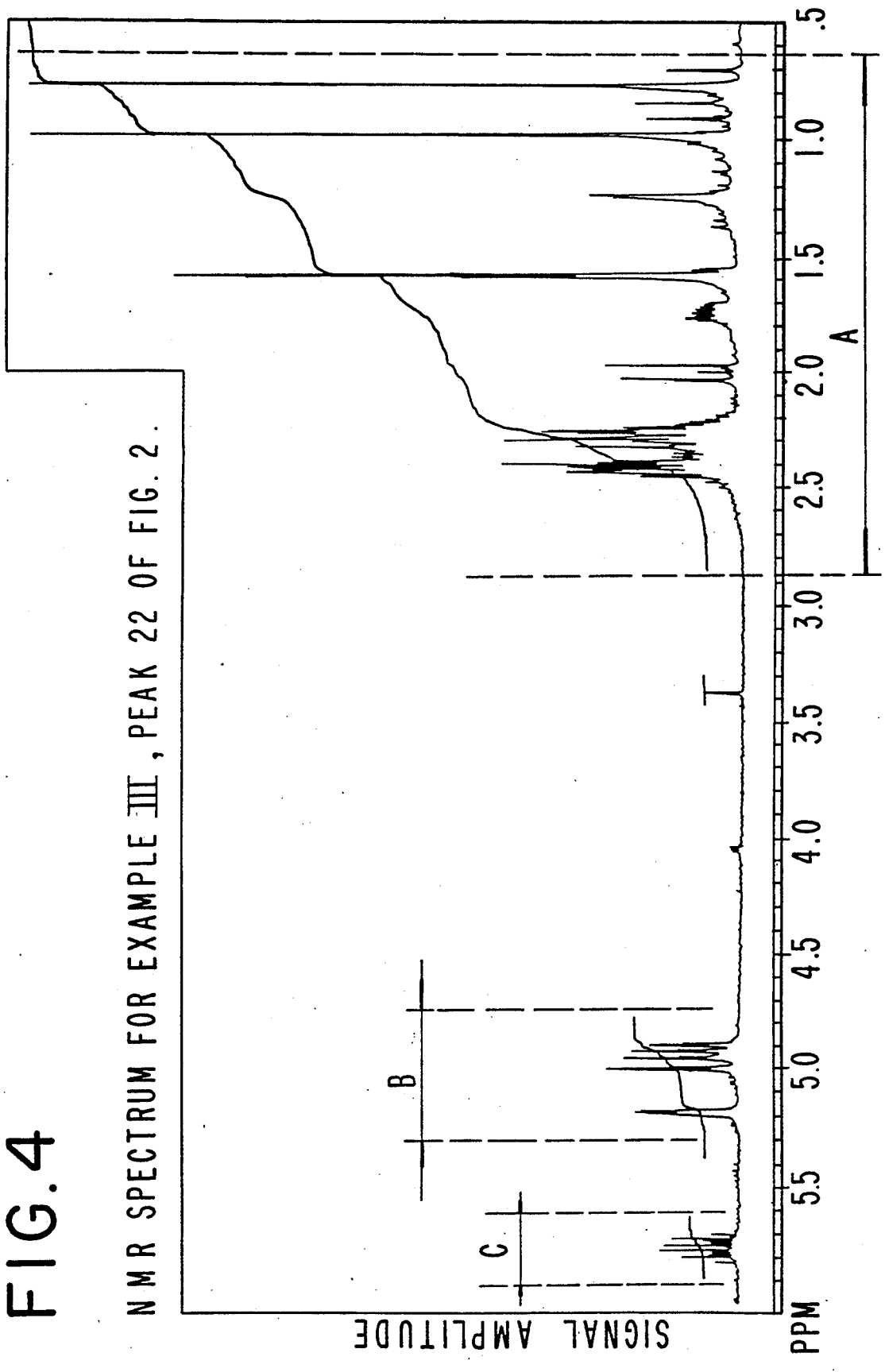

FIG. 4 is the NMR spectrum for the peak indicated by reference numeral 22 on FIG. 2 and is for the compound having the structure:

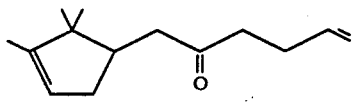

prepared according to Example III.

FIGS. 4A, 4B and 4C represent details of enlarged sections of the NMR spectrum of FIG. 4 denoted as "A", "B" and "C" on FIG. 4.

FIG. 5 is the infra-red spectrum for the mixture of compounds prepared according to Example III having the structures:

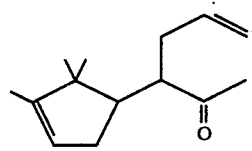

and

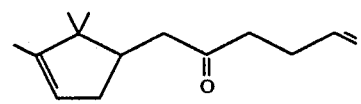

Figure 6:
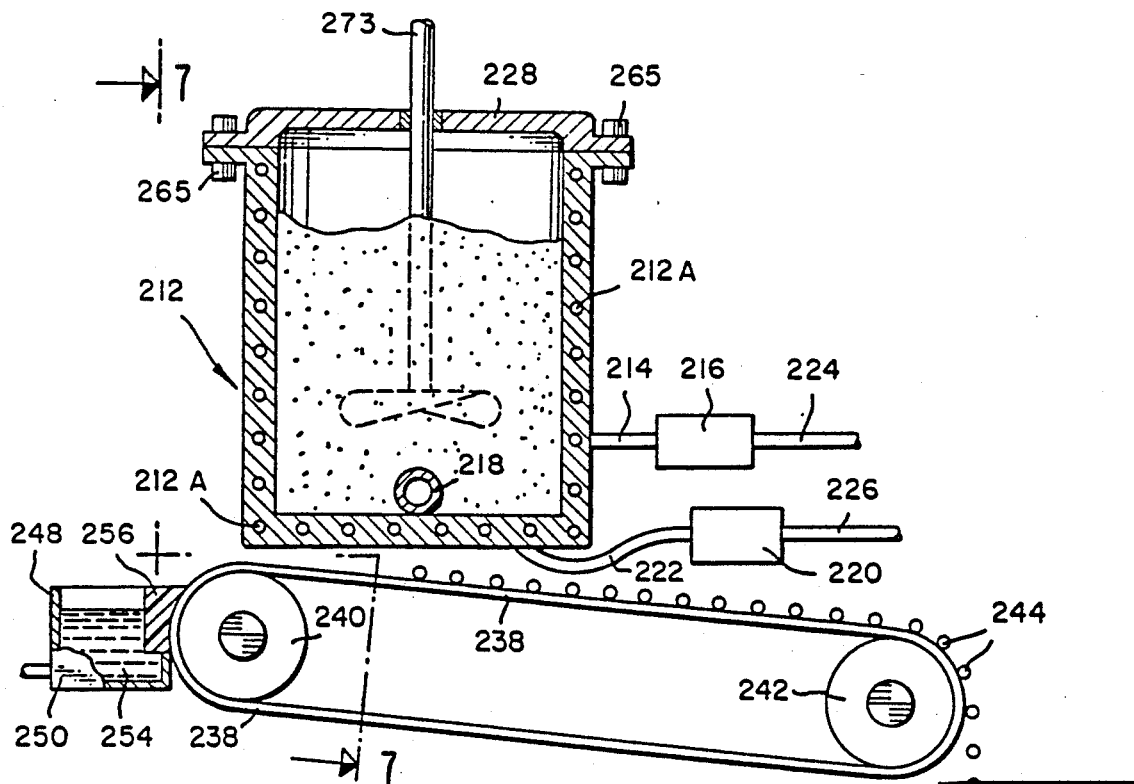

FIG. 6 represents a cutaway side elevation view of apparatus used in forming perfumed polymers which contain embedded therein at least one of the 2,2,3-trimethylcyclopentenyl acetone derivatives of our invention.

Figure 7:
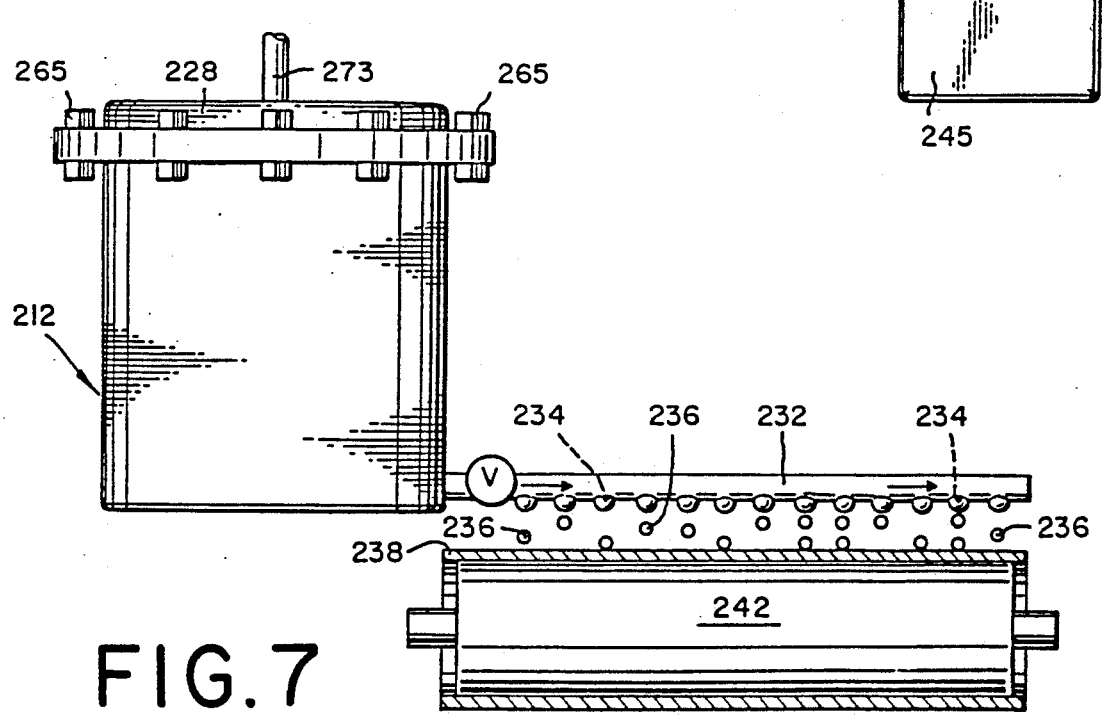

FIG. 7 is a front view of the apparatus of FIG. 6 looking in the direction of the arrows.

DETAILED DESCRIPTION OF THE DRAWINGS

Figure 1:
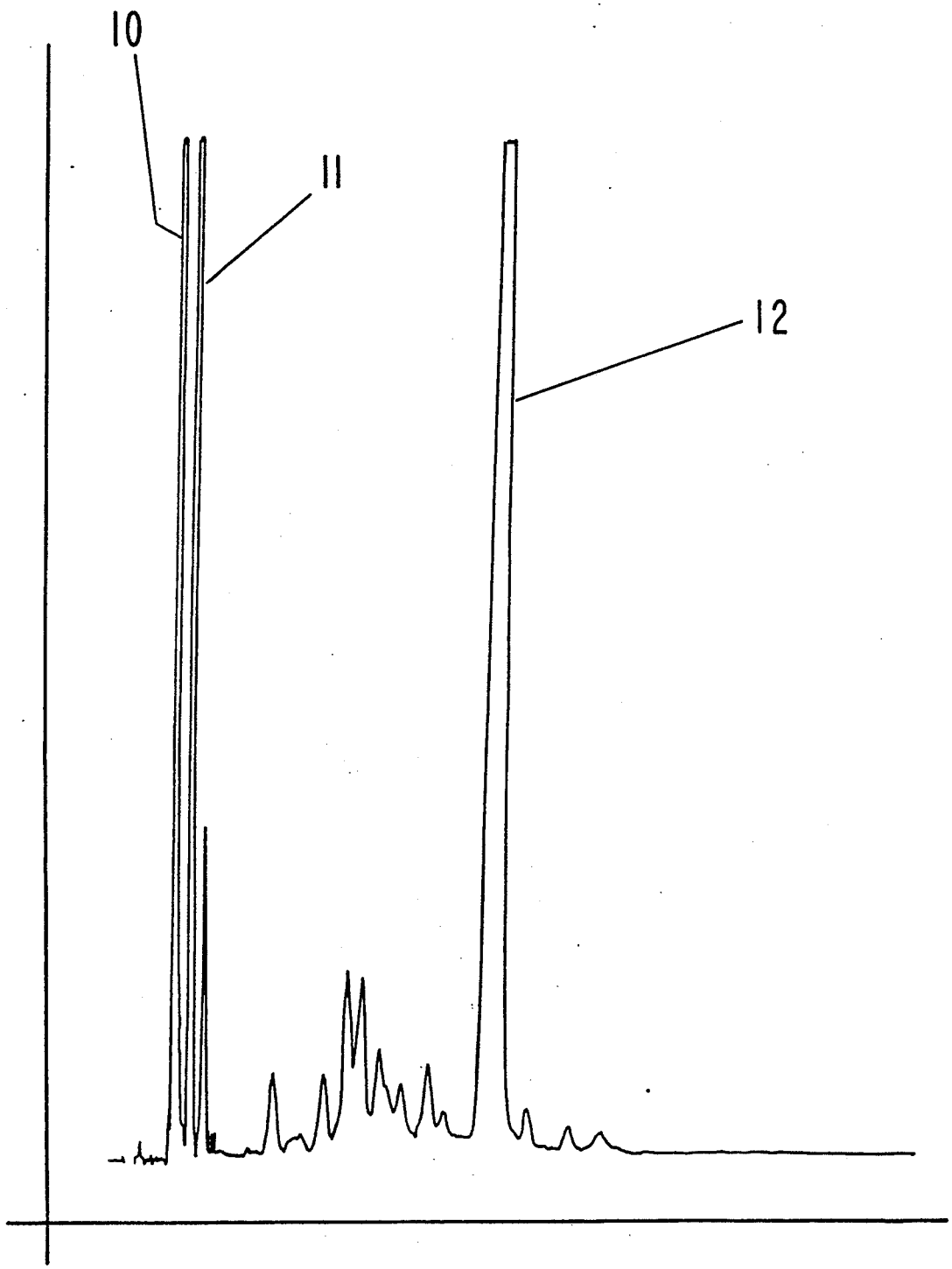
FIG. 1 is the GLC profile for the reaction product of Example II containing the compound having the structure.

FIG. 1 is the GLC profile for the reaction product of Example II (conditions:SE-30 column programmed at 150°-220° C. at 8° C. per minute. The peaks indicated by reference numerals 10 and 11 are the peaks for the solvents used in the reaction. The peak indicated by reference numeral 12 is the peak for the compound having the structure:

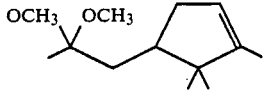

FIG. 2 is the GLC profile for the reaction product of Example III (conditions:S-1 column programmed at 150°-220° C. at 8° C. per minute. The peak indicated by reference numeral 21 is the peak for the compound having the structure:

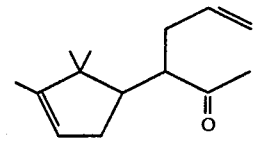

The peak indicated by reference numeral 22 is the peak for the compound having the structure:

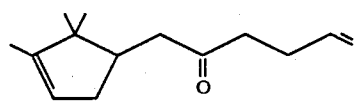

FIG. 3 is the NMR spectrum for the peak indicated by reference numeral 21 on FIG. 2. The section of the NMR spectrum denoted by the "A" is set forth in detail in FIG. 3A. The section of the NMR spectrum of FIG. 3 denoted by the "B" is set forth in detail in FIG. 3B. The section of the NMR spectrum of FIG. 3 denoted by the "C" is set forth in FIG. 3C.

FIG. 4 is the NMR spectrum for the peak indicated by reference numeral 22 of FIG. 2 for the compound having the structure:

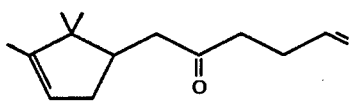

Referring to FIGS. 6 and 7 there is provided a process for forming scented polymer elements (wherein the polymer may be a thermoplastic polymer such as low density polyethylene or polypropylene or copolymers of ethylene and vinyl acetate or mixtures of polymers and copolymers such as copolymers of ethylene and vinyl acetate and polyethylene) such as pellets useful in the formation of plastic particles useful in fabricating certain articles which may be perfumed. The process comprises heating the polymer or mixture of polymers to the melting point of said polymer or mixture of polymers, e.g., 250° C. in the case of low density polyethylene. The lowermost portion of the container 212 is maintained at a slightly lower temperature and the material in the container is taken off at such location for delivery through the conduit. Thus, referring to FIGS. 6 and 7, in particular, the apparatus used in producing such elements comprises a device for forming the polymer containing perfume, e.g. polyethylene or polyethylene-polyvinyl acetate or mixtures of same or polypropylene, which comprises a vat or container 212 into which the polymer taken alone or in admixture with other copolymers and the perfuming substance which is a mixture of at least one of the 2,2,3-trimethylcyclopentenyl acetone derivatives of our invention and other compatible perfumes (if desired) is placed. The container is closed by means of an air-tight lid 228 and clamped to the container by bolts 265. A stirrer 273 traverses the lid or cover 228 in air-tight manner and is rotatable in a suitable manner. A surrounding cylinder 212 having heating coils 212A which are supplied with electric current through cables 214 and 222 from rheostats or controls 216 or 220 is operated to maintain the temperature inside the container 212 such that the polymer in the container will be maintained in the molten or liquid state. It has been found advantageous to employ polymers at such a temperature that the viscosity will be in the range of 90–100 sayboldt seconds. The heater 218 is operated to maintain the upper portion of the container 212 within a temperature range of, for example, 220°–270° C. in the case of low density polyethylene. The bottom portion of the container 212 is heated by means of heating coils 212A regulated through the control 220 and the control 216 connected thereto through connecting wires 222 and 214 respectively to maintain the lower portion of the container 212 within a temperature range of 220°–270° C.

Thus, the polymer or mixture of polymers added to the container 212 is heated from 10–12 hours, whereafter the perfume composition or perfume material which contains at least one of the 2,2,3-trimethylcyclopentenyl acetone derivatives of our invention is quickly added to the melt. Generally, about 10–45% by weight of the resulting mixture of the perfumery substance containing at least one of the 2,2,3-trimethylcyclopentenyl acetone derivatives of our invention is added to the polymer.

After the perfume material is added to the container 212, the mixture is stirred for a few minutes, for example, 5–15 minutes and maintained within the temperature ranges indicated previously by the heating coil 212A. The controls 216 and 220 are connected through cables 224 and 226 to a suitable supply of electric current for supplying the power for heating purposes.

Thereafter, the valve "V" is opened permitting the mass to flow outwardly through conduit 232 having a multiplicity of orifices 234 adjacent to the lower side thereof. The outer end of the conduit 232 is closed so that the liquid polymer in intimate admixture with the composition containing at least one of the 2,2,3-trimethylcyclopentenyl acetone derivatives of our invention taken alone or taken further together with other perfume substances will continuously drop through the orifices 234 downwardly from the conduit 232. During this time, the temperature of the polymer intimately admixed with the perfumery substance in the container 212 is accurately controlled so that a temperature in the range of from about 240°–250° C., for example, (in the case of low density polyethylene) will exist in the conduit 232. The regulation of the temperature through the controls 216 and 220 is essential in order to insure temperature balance to provide for the continuous dripping or dropping of molten polymer intimately admixed with the perfume substance (containing at least one of the 2,2,3-trimethylcyclopentenyl acetone derivatives of our invention and, if desired, other materials compatible with one of said 2,2,3-trimethylcyclopentenyl acetone derivatives of our invention) through the orifices 234 at a rate which will insure the formation of droplets 236 which will fall downwardly onto a moving conveyor belt 238 caused to run between conveyor wheels 240 and 242 beneath the conduit 232.

When the droplets 236 fall onto the conveyor 238, they form pellets 244 which harden almost instantaneously and fall off the end of the conveyor 238 into a container 250 which is advantageously filled with water 254 or some other suitable cooling liquid 254 to insure the rapid cooling of each of the pellets 244. The pellets are then collected from the container 250 and utilized for the formation of other functional products, e.g., garbage bags and the like.

THE INVENTION

The present invention provides 2,2,3-trimethylcyclopentenyl acetone derivatives defined according to at least one of the structures:

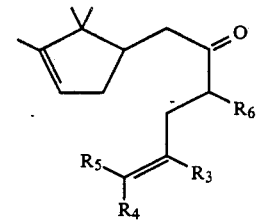

and

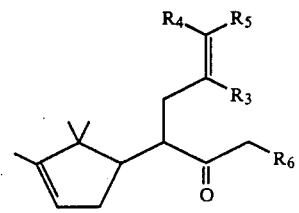

as well as ketal intermediates defined according to the structure:

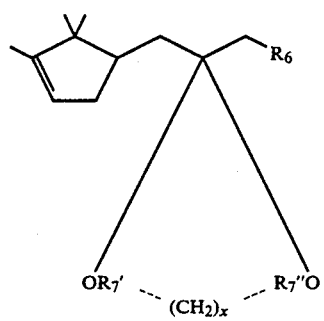

wherein $R_3$, $R_4$, and $R_5$ are the same or different hydrogen or methyl; $R_6$ represents hydrogen methyl, ethyl, propyl or isopropyl; x is 0, 1 or 2; $R_7'$ and $R_7''$ represents the same or different methyl or ethyl or $R_7'$, $(CH_2)_x$ and $R_7''$ taken together represent $C_2$-$C_6$ alkylene. The 2,2,3-trimethylcyclopentenyl acetone derivatives of our invention defined above are capable of augmenting or enhancing the aroma and/or taste of consumable materials including but not limited to perfume compositions, colognes and (perfumed articles (including but not limited to soaps, anionic, cationic, nonionic or zwitterionic detergents, fabric softener compositions, fabric softener articles, optical brighteners, perfumed polymers, hair preparations and the like) thus fulfilling a need in the field of perfumery as well as detergent, cologne, fabric softener and cosmetic manufacturer. The 2,2,3-trimethylcyclopentenyl acetone derivatives of our invention are long lasting and substantive and give rise to sweet, green, fruity, pineapple, galbanum and geranium aromas with sweet, fruity, pineapple and green topnotes.

The 2,2,3-trimethylcyclopentenyl acetone derivatives of our invention may be prepared using as a starting material the nitrile having the structure:

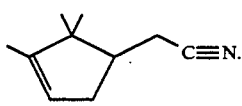

this nitrile is reacted with an organometallic compound having the structure:

wherein $R_6$ represents hydrogen, methyl, ethyl, propyl or isopropyl; and M represents MgX or Li; and wherein X represents chloro or bromo. The reaction between the compounds having the structure:

and the nitrile having the structure:

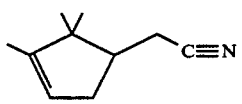

is shown thusly:

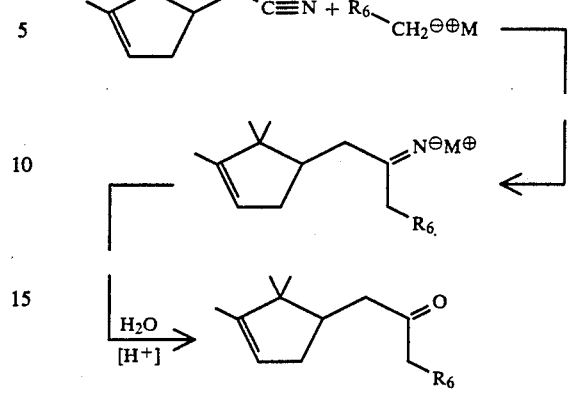

Thus, the intermediate having the structure

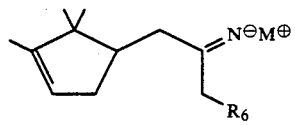

is formed and this intermediate is reacted with water in the presence of acid to produce the ketone having the structure:

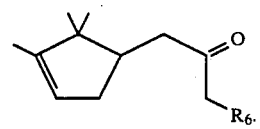

The ketone having the structure:

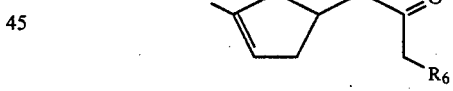

is then reacted with a ketal-producing reagent which may be for example, a compound having the structure:

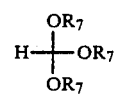

(a trialkyl orthoformate such as trimethyl or triethyl orthoformate) or a compound having a structure:

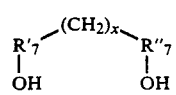

The formation of the ketal from the ketone having the structure:

is shown thusly:

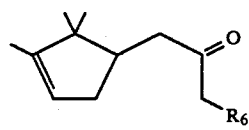

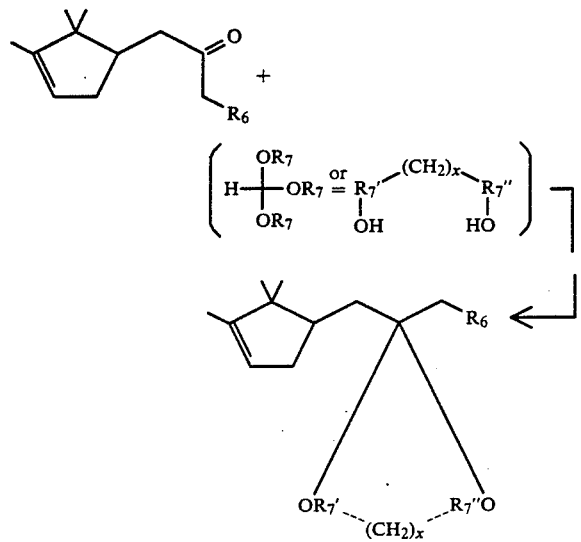

The resulting ketal is then reacted with an allylic alcohol (such as prenyl alcohol) having the structure:

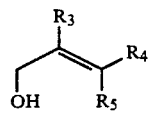

according to the reaction:

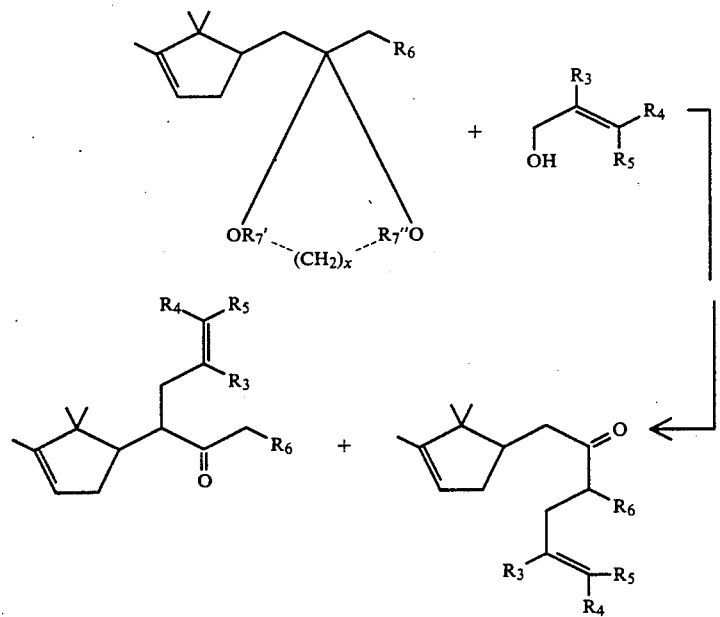

wherein x represents 0, 1 or 2 and wherein the dashed lines represent carbon-carbon single bonds when x is 1 or 2 or no bonds when x is 0. Also, the groups are 7', $(CH_2)_x$ and $R_7''$ taken together may represent $C_2$–$C_6$ alkylene.

The above process is unexpected, unobvious and advantageous in that it yields a ratio of the compound having the structure:

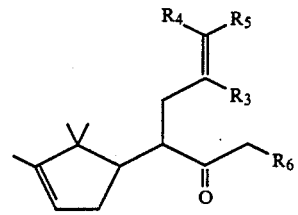

to compound having the structure:

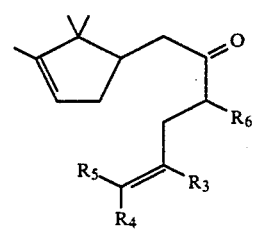

of from about 90:10 down to about 80:20. The resulting compounds having the structures:

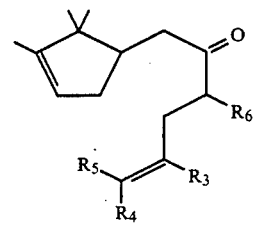

and

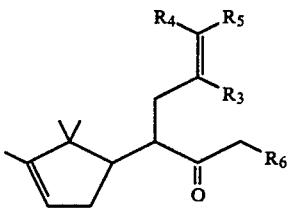

can, of course, be easily separated using commercial preparative chromotographic techniques.

In that case where M represents MgBr, the first of the above reaction sequences is shown thusly:

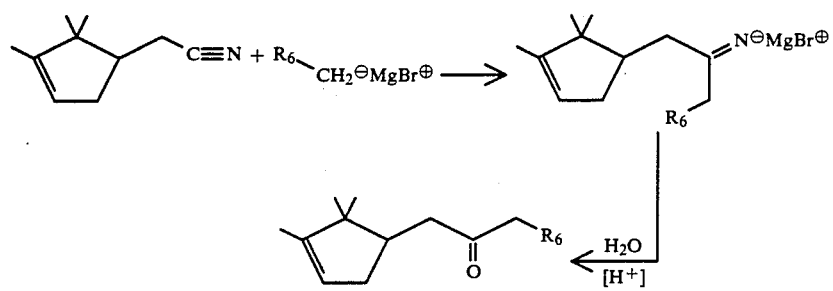

when $R_7$ is methyl, the second of the above reaction sequences is shown thusly:

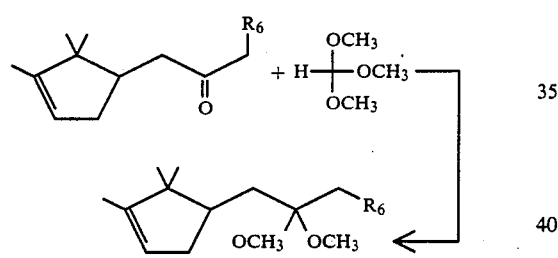

and the third of the reaction sequences set forth supra is shown thusly:

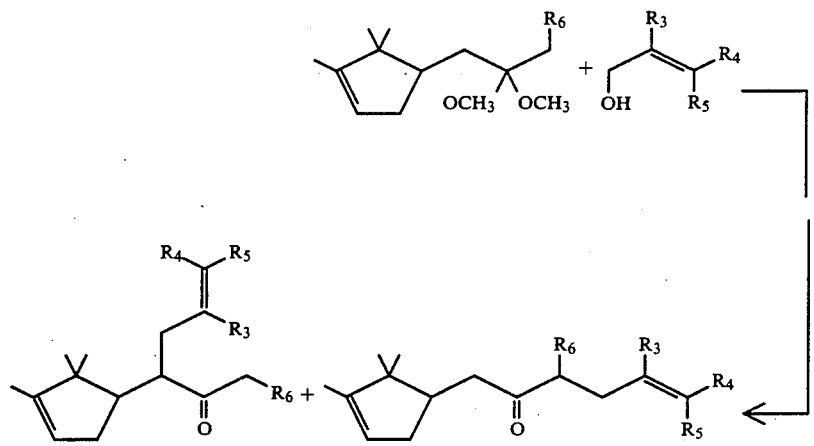

Preferably, the compounds produced according to the foregoing process and compositions produced according to the foregoing process are as follows:

(i) the mixture of compounds having the structures:

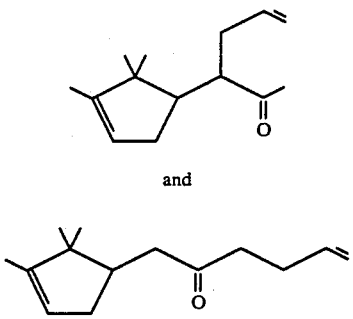

(ii) the mixture of compounds having the structures:

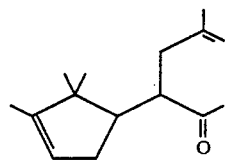

and

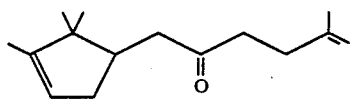

(iii) the mixture of compounds having the structures:

-continued

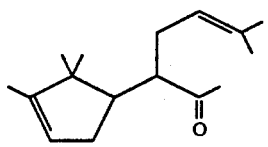

and

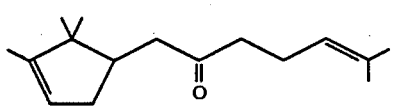

(iv) the compound having the structure:

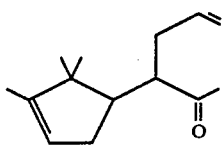

(v) the compound having the structure:

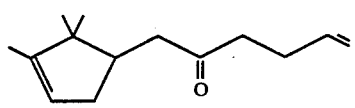

(vi) the compound having the structure:

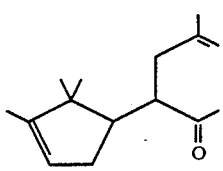

(vii) the compound having the structure:

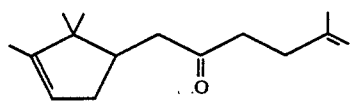

(viii) the compound having the structure:

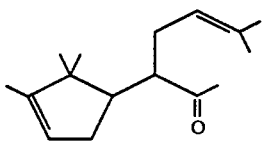

and (ix) the compound having the structure:

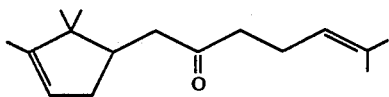

With respect to the reaction sequence:

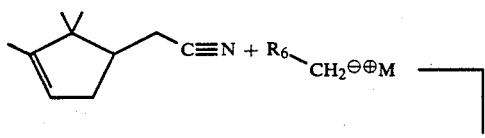

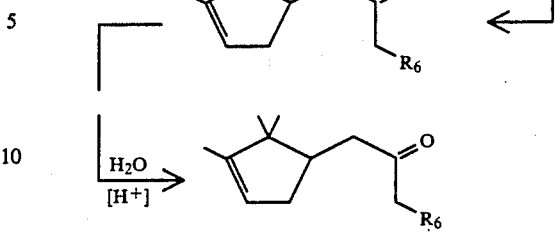

the reaction of the alkyl organometallic compound with the nitrile is carried out at low temperatures, e.g., about 0° C. up to about 10° C. preferably in the presence of an inert solvent such as diethyl ether or tetrahydrofuran. The mole ratio of organometallic compound to nitrile may vary from about 1:1 up to about 1.5:1. The imine salt is then hydrolyzed to the ketone using mineral acid such as dilute hydrochloric acid and the like in the presence of water at approximately room temperature.

With reference to the formation of the ketals according to the reaction sequence:

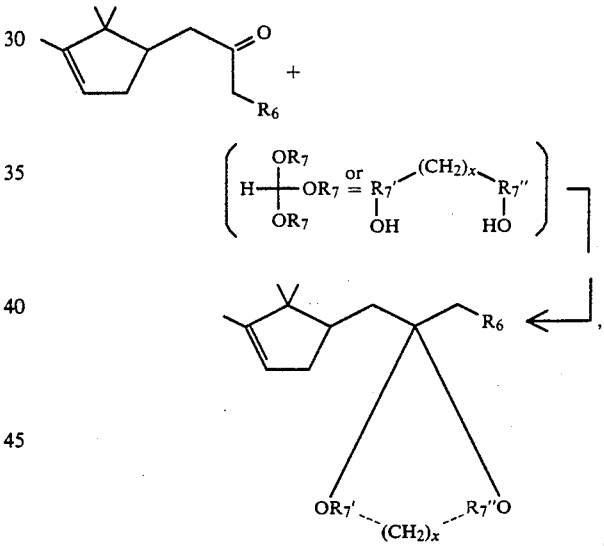

this reaction is carried out in the presence of protonic acid (a catalytic quantity) such as paratoluene sulfonic acid or methane sulphonic acid in the presence of a compatible solvent (methyl alcohol when trimethylorthoformate is used as the reagent). The mole ratio of, for example, trimethylorthoformate:ketone is preferably about 2:1 (since 2 methyl groups are needed for every ketone moity). The reaction is carried out at a temperature in the range of from about 10° C. up to about 20° C. The molar concentration of acid catalyst in the reaction mass is between about 0.2% up to about 0.5% based on the other reactants. The actual concentration of acid catalyst may vary from about 0.02 moles per liter up to about 0.05 moles per liter. At the end of the reaction the reaction mass is distilled and the ketals having the structure:

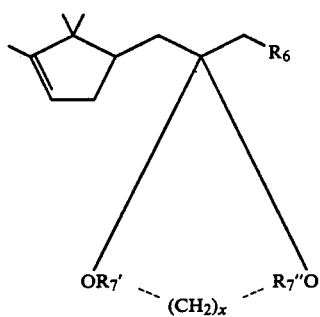

may be recovered and used "as is" for their perfumery properties or they may be further reacted with compounds defined according to the structure:

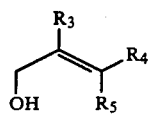

as shown in the reaction sequence:

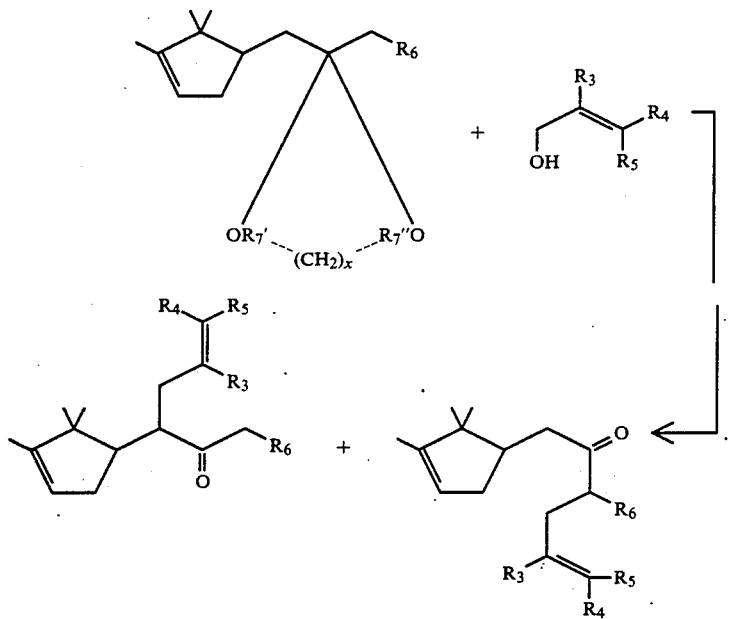

The mole ratio of allylic alcohol:ketal is about 2:1 with a slight excess of ketal being used. The reaction is preferably carried out using a weak acid catalyst such as citric acid. When the citric acid is used, the concentration of citric acid in the reaction mass is between 0.4 and 0.6 grams per kilogram of reaction mass. The reaction is carried out at reflux conditions, preferably between about 90° C. and 100° C. At the end of the reaction, the reaction product is distilled from the reaction mass preferably using vacuum distillation techniques.

Examples of reaction products and their properties are set forth in the following Table I.

TABLE I

| Identification of Reaction Product | Perfumery Property |
|---|---|
| 82:15 (mole:mole) mixture of compounds having the structures: <br><br> and <br><br> prepared according to Example III. | A sweet, green, fruity, pineapple and galbanum aroma profile with sweet, fruity, pineapple and green topnotes. |
| The compound having the structure: <br><br> prepared according to Example III. | A galbanum, green, geranium, fruity and pineapple aroma profile. |

The 2,2,3-trimethylcyclopentenyl acetone derivatives of our invention and one or more auxiliary perfume ingredients, including, for example, alcohols, aldehydes, ketones other than the 2,2,3-trimethylcyclopentenyl acetone derivatives of our invention, terpenic hydrocarbons, nitriles, esters, lactones, ethers other than the ketals of our invention, natural essential oils and synthetic essential oils may be admixed so that the combined odors of the individual components produce a pleasant and desired fragrance particularly and preferably in the amber, cedarwood and patchouli area.

Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling, fresh smelling materials.

In perfume compositions, it is the individual components which contribute to their particular olfactory characteristics, however, the overall sensory effect of the perfume compositions will be at least the sum total of the effects of each of the ingredients. Thus, one or more of the 2,2,3-trimethylcyclopentenyl acetone derivatives of our invention can be used to alter, modify, or enhance the aroma characteristics of a perfume composition, for example, by utilizing or moderating the olfactory reaction contributed by another ingredient in the composition.

The amount of one or more of the 2,2,3-trimethylcyclopentenyl acetone derivatives of our invention which will be effective in perfume compositions as well as in perfumed articles (e.g. anionic, cationic, nonionic or zwitterionic solid or liquid detergents, soaps, fabric softener compositions, drier-added fabric softener articles, optical brightener compositions, perfumed polymers and textile sizing agents) and colognes depends on many factors, including the other ingredients, their amounts and the effects which are desired. It has been found that perfume compositions containing as little as 0.05% of one or more of the 2,2,3-trimethylcyclopentenyl acetone derivatives of our invention prepared in accordance with the process set forth supra and less than 50% of one or more of the 2,2,3-trimethylcyclopentenyl acetone derivatives of our invention or even less, e.g., 0.005% can be used to impart, augment or enhance sweet, green, fruity, pineapple, galbanum and geranium aroma profiles with sweet, fruity, pineapple and green topnotes to soaps, cosmetics, solid or liquid anionic, cationic, nonionic or zwitterionic detergents, fabric softener compositions, fabric softener articles, optical brightener compositions, textile sizing compositions, perfumed polymers or other products. The amount employed can range up to 70% of the fragrance components and will depend on considerations of cost, nature of the end product, the effect desired on the finished product and the particular fragrance sought.

One of more of the 2,2,3-trimethylcyclopentenyl acetone derivatives of our invention are useful (taken alone or with other ingredients) in perfume compositions as (an) olfactory component(s) in detergents and soaps, space odorants and deodorants, perfumes, colognes, toilet water, bath preparations, such as creams, deodorants, hand lotions and sun screens; powders, such as talcs, dusting powders, face powders and perfumed polymers and articles of manufacture produced from said perfumed polymers, e.g., garbage bags, children's toys and the like. When used as (an) olfactory component(s) as little as 0.2% of one or more of the 2,2,3-trimethylcyclopentenyl acetone derivatives of our invention will suffice to impart, augment or enhance sweet, green, fruity, pineapple, galbanum and geranium aroma profiles with sweet, fruity, pineapple and green topnotes to spicy, amber and patchouli formulations. Generally no more than 6% of one or more of the 2,2,3-trimethylcyclopentenyl acetone derivatives of our invention based on the ultimate end product are required in the perfumed article composition. Accordingly, the range of one or more of the 2,2,3-trimethylcyclopentenyl acetone derivatives of our invention in the perfumed article is from about 0.2% by weight of one or more of the 2,2,3-trimethylcyclopentenyl acetone derivatives of our invention up to about 6% by weight of one or more of the 2,2,3-trimethylcyclopentenyl acetone derivatives of our invention based on the total weight of perfumed articles.

In addition, the perfume or fragrance composition of our invention can contain a vehicle for one or more of the 2,2,3-trimethylcyclopentenyl acetone derivatives of our invention. The vehicle can be a liquid, such as a non-toxic alcohol, e.g., ethyl alcohol, a non-toxic glycol, e.g., propylene glycol or the like. The carrier can also be an absorbent solid, such as a gum (e.g., gum arabic or xanthan gum) or components for encapsulating the composition (such as gelatin as by coacervation or such as, an urea formaldehyde prepolymer forming a capsule shell around a liquid perfume center.

Our invention also relates to the utilization of control release technology for the controlled release of perfumes into gaseous environments from polymers such as mixtures of epsilon polycaprolactone polymers and polyethylene according to the disclosure of U.S. Pat. No. 4,715,981 at columns 10, 11 and 12 of the specification, the specification for which is incorporated by reference herein.

The following Examples I, II and III serve to provide a process for preparing one or more of the 2,2,3-trimethylcyclopentenyl acetone derivatives as well as the ketal intermediate which is also useful in perfumery. The examples following Example III are illustrative of the organoleptic utilities of one or more of the 2,2,3-trimethylcyclopentenyl acetone derivatives of our invention.

All parts and percentages given herein are by weight unless otherwise specified.

EXAMPLE I

PREPARATION OF CAMPHOLENIC METHYL KETONE

Reaction

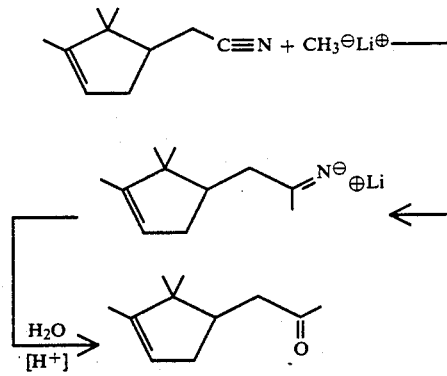

Into a 12 liter reaction flask equipped with a jackomatic and a dry ice bath are placed 5.6 moles of methyl lithium in 4 liters of diethyl ether under a nitrogen blanket. The solution is cooled to 2° C. and over a period of 2.5 hours while maintaining the temperature at 2°–5° C., 5.33 moles (958 grams) of the nitrile having the structure:

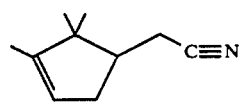

is fed into the reaction mass.

The reaction mass is aged for a period of 3 hours.

The reaction mass is then quench using 750 ml of 1 molar hydrochloric acid solution.

One liter of water was then added and the reaction mass is then stirred for 1.5 hours. At the end of the 1.5 hour period the reaction product, ammonia ceases to evolve.

The reaction mass now exists in two phases an organic phase and an aqueous phase. The organic phase is washed with 500 ml brine (saturated sodium chloride) and filtered through anhydrous magnesium sulfate. During the filtration most of the ether boils off. The reaction mass is then rushed over on a one plate distillation column yielding 398 grams of product.

EXAMPLE II

PREPARATION OF CAMPHOLENIC METHYL KETONE DIMETHYL KETAL REACTION

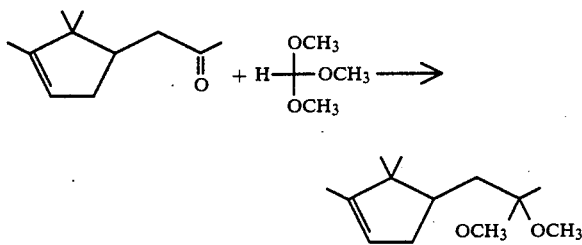

Into a 3 liter reaction flask equipped with dry ice bath/isopropyl alcohol bath is placed 2.76 moles (458 grams) of the ketone prepared according to Example I.

The temperature of the ketone is lowered to 20° C. and the flask is then charged with 5.52 moles (585 grams) of trimethylorthoformate. The resulting reaction mass is cooled to 10° C. and 0.03 moles (5.7 grams) of paratoluene sulfonic acid in 500 ml methanol is added to the reaction mass while maintaining the reaction mass at 10° C.

The reaction mass is then permitted to warm to 27° C. and is stirred at 27° C. for a period of 6 hours.

2.46 grams (0.03 moles) of sodium acetate is then added to reaction mass in order to neutralize the paratoluene sulfonic acid catalyst. The reaction mass is stirred until one phase exists.

7.5 grams (0.03 moles) of pyridinium tosylate is added to the reaction mass.

The reaction mass is then heated to reflux (62°-70° C. and aged for 7 hours at reflux conditions. The reaction mass is then cooled to room temperature and 2.46 grams (0.03 moles) of sodium acetate is added.

18 grams of 4% AMBERLYST A-15(R) ion exchange resin is added. The reaction mass is then aged for a period of 12 hours at room temperature. The reaction mass is then heated to 40° C. and aged for a period of 11 hours. The reaction mass is then filtered and 10 grams of sodium acetate are added. The reaction mass is then distilled on a one plate "rush over" column yielding the following fractions:

| Fraction No. | Vapor Temp. (°C.) | Liquid Temp. (°C.) | Vacuum mm/Hg. Pressure |
|---|---|---|---|
| 1 | 65/73 | 76/91 | ATM/2.3 |
| 2 | 72 | 91 | 4.0 |
| 3 | 73 | 90 | 3.3 |
| 4 | 74 | 91 | 3.28 |
| 5 | 77 | 93 | 3.28 |
| 6 | 85 | 101 | 3.28 |

NMR and IR spectra confirm that the reaction product has the structure:

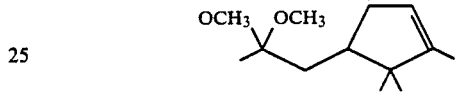

FIG. 1 is the GLC profile for the reaction mass prior to distillation. The peak indicated by reference numeral 12 is the peak for the compound having the structure:

| Fraction No. | Vapor Temp. (°C.) | Liquid Temp. (°C.) | Vacuum mm/Hg. Pressure |
|---|---|---|---|
| 1 | 65/73 | 76/91 | ATM/2.3 |
| 2 | 72 | 91 | 4.0 |
| 3 | 73 | 90 | 3.3 |
| 4 | 74 | 91 | 3.28 |
| 5 | 77 | 93 | 3.28 |
| 6 | 85 | 101 | 3.28 |

The peaks indicated by reference numerals 10 an 11 are the peaks for the solvent used in the reaction.

EXAMPLE III

PREPARATION OF ALLYL-SUBSTITUTED 2,2,3 TRIMETHYLCYCLOPENT-b 3 -ENYL ACETONE

Reaction

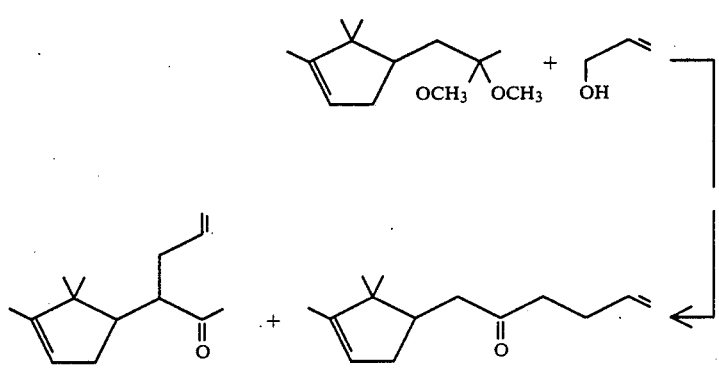

Into a 2 liter reaction flask equipped with stirrer, thermometer, reflux condenser and hating mantle are placed 470 grams (2.4 moles) of the compound having the structure:

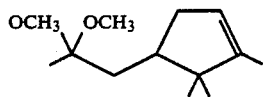

and 755 grams (4.4 moles) of allyl alcohol and 0.5 grams of citric acid and 1 liter of methyl alcohol.

The reaction mass is heated to reflux with stirring (95° C.) and the methyl alcohol distilled off.

After all of the methyl alcohol is stripped off, a GLC profile indicated 70% conversion.

The resulting reaction product is distilled on a fractional distillation column yielding the following fractions:

| Fraction No. | Vapor Temp. (°C.) | Liquid Temp. (°C.) | Vacuum mm/Hg. Pressure | Weight of Fraction |
|---|---|---|---|---|
| 1 | 80/108 | 122/125 | 10/10.4 | 21 |
| 2 | 107 | 125 | 10.4 | 6 |
| 3 | 116 | 125 | 9.82 | 12 |
| 4 | 121 | 125 | 9.90 | 10 |
| 5 | 123 | 125 | 9.90 | 12 |
| 6 | 123 | 125 | 9.90 | 7 |
| 7 | 122 | 125 | 9.90 | 5 |
| 8 | 125 | 126 | 9.90 | 9 |
| 9 | 124 | 126 | 9.90 | 8 |
| 10 | 124 | 126 | 9.95 | 7 |
| 11 | 125 | 127 | 9.95 | 9 |
| 12 | 125 | 127 | 9.95 | 8 |
| 13 | 125 | 127 | 9.95 | 6 |
| 14 | 125 | 127 | 9.9 | 11 |
| 15 | 125 | 140 | 10.0 | 12 |
| 16 | 125 | 140 | 10.0 | 12 |
| 17 | 125 | 140 | 10.0 | 31 |
| 18 | 125 | 140 | 10.0 | 12 |
| 19 | 125 | 140 | 10.0 | 25 |
| 20 | 125 | 140 | 10.0 | 31 |
| 21 | 127 | 140 | 10.0 | 29 |

The resulting product is a mixture of compounds having the structures:

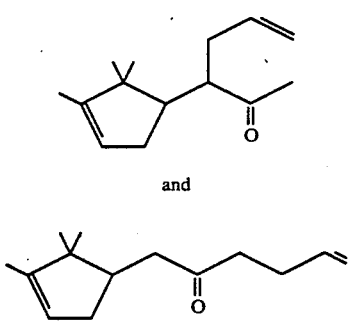

and with the ratio of the compound having the structure:

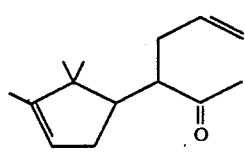

to the compound having the structure:

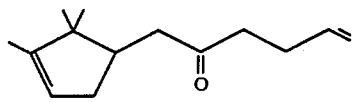

being 82:15 (mole ratio) (bulked distillation fractions 5-17).

FIG. 2 is the GLC profile for the reaction product prior to distillation. The peak indication by reference numeral 21 is the peak for compound having the structure:

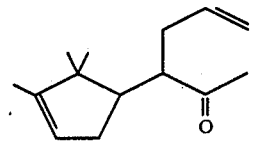

The peak indicated by reference numeral 22 is the peak for the compound having the structure:

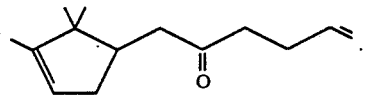

FIG. 3 is the NMR spectrum for peak 21 of FIG. 2 for the compound having the structure:

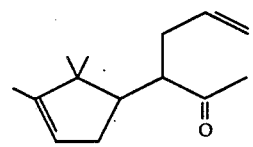

FIG. 4 is the NMR spectrum for peak 22 of FIG. 2 for the compound having the structure:

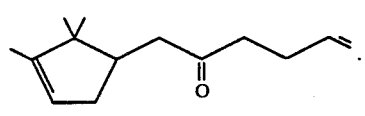

The compound having the structure:

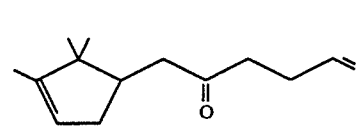

has an galbanum, green, geranium, fruity and pineapple aroma profile. The mixture of compounds having the structures:

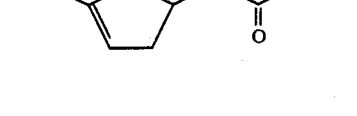

and

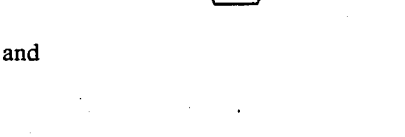

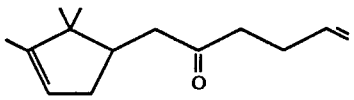

(mole ratio 82:15) has a sweet, green, fruity, pineapple and galbanum aroma profile with sweet, fruity, pineapple and green topnotes.

EXAMPLE IV

PREPARATION OF PINE FRAGRANCE

The following pine fragrance formulation is prepared:

TABLE I

| Ingredients | Parts by Weight |
| --- | --- |
| Isobornyl acetate | 100 |
| Camphor | 10 |
| Alpha-Terpineol | 25 |
| Fir balsam absolute (50% in diethyl phthalate) | 20 |
| Coumarin | 4 |
| Linalool | 30 |
| Fenchyl alcohol | 10 |
| Anethole | 12 |
| Lemon terpenes washed | 50 |
| Borneol | 5 |
| Galbanum oil | 5 |
| Turpentine Russian | 150 |
| Eucalyptol | 50 |
| 2,2,6-trimethyl-1-cyclohexene-1-carboxaldehyde | 12 |
| Maltol (1% in diethyl phthalate) | 15 |
| Mixture of compounds having the structures: 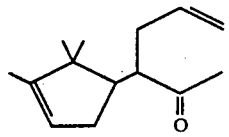 and <br>(mole ratio 15:82) produced according Example III, bulked distillation fractions 5-17; | 28 |

The mixture of compounds having the structures:

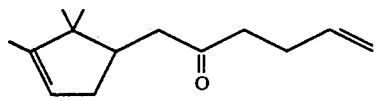

and

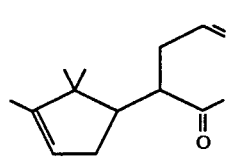

(mole ratio 15:82) produced according to Example I, bulked distillation fractions 5-17 imparts to the pine formulation an intense and substantive sweet, green, fruity, pineapple and galbanum undertones with sweet, fruity, pineapple and green topnotes. Accordingly, the perfume composition of Example IV can be described as:

"piney with sweet, green, fruity, pineapple and galbanum undertones and sweet, fruity, pineapple and green topnotes".

EXAMPLE V

PREPARATION OF COSMETIC POWDER COMPOSITIONS

Cosmetic powder compositions are prepared by mixing in a ball mill 100 grams of talcum powder with 0.25 grams of each of the substances set forth in Table II below. Each of the cosmetic powder compositions has an excellent aroma as described in Table II below:

TABLE II

| Substance | Aroma Description |
| --- | --- |
| The mixture of compounds having the structures: <br>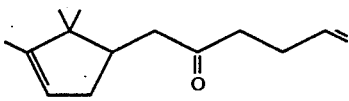<br> and <br>(mole ratio 15:82) prepared according to Example III, bulked distillation fractions 5-17; | A sweet, green, fruity, pineapple and galbanum aroma profile with sweet, fruity, pineapple and green topnotes. |
| The compound having the structure: | A galbanum, green, geranium, fruity and pineapple aroma profile. |
| Perfume composition of Example IV | A piney with sweet, green, fruity, pineapple and galbanum undertones and sweet, fruity, pineapple and green topnotes. |

EXAMPLE VI

PERFUMED LIQUID DETERGENT

Concentrated liquid detergents with aromas as set forth in Table II of Example V (which detergents are prepared from Lysine salt of n-dodecyl benzene sulfonic acid as more specifically described in U.S. Pat. No. 3,948,818 issued on Apr. 6, 1976, the specification for which is incorporated by reference herein) are prepared containing each of the substances set forth in Table II of Example V, supra. They are prepared by adding and homogeneously mixing the appropriate quantity of perfumery substance as set forth in Table II of Example V in liquid detergent The detergents all possess aromas as set forth in Table II of Example V, the intensity increasing with greater concentrations of perfumery substance of Table II of Example V, supra.

EXAMPLE VII

PREPARATION OF A COLOGNE AND HANDKERCHIEF PERFUME

The perfume substances of Table II of Example V, supra, are incorporated into colognes at concentrations of 1.5%, 2.0%, 2.5%, 3.0% and 4.0% in 80%, 85% and 90% aqueous ethanol; and into handkerchief perfume compositions at concentrations of 10%, 15%, 20%, 25% and 30% (in 85%, 90% and 95% aqueous ethanol). Distinct and definite aromas as set forth in Table II of Example V are imparted to the cologne and to the handkerchief perfume compositions.

EXAMPLE VIII

PREPARATION OF A DETERGENT COMPOSITION

A total of 100 grams of a detergent powder (a nonionic detergent powder containing a proteolytic enzyme prepared according to Example II of Canadian Patent 985,190 issued on Mar. 9, 1976, the disclosure of which is incorporated by reference herein) is mixed with 0.15 grams of each of the substances set forth in Table II of Example V, supra until substantially homogeneous compositions are obtained. These compositions have excellent aromas as set forth in Table II of Example V.

EXAMPLE IX

PREPARATION OF SOAP

Each of the perfumery substances of Table II of Example V are incorporated into soap (LVU-1) at 0.1% by weight of each substance. After two weeks in the oven at 90° F. each of the soaps showed no visual effect from the heat. Each of the soaps manifested an excellent aroma as set forth in Table II of Example V, supra.

EXAMPLE X

PREPARATION OF SOAP COMPOSITION

One hundred grams of soap chips (IVORY ®, registered trademark of the Procter & Gamble Company of Cincinnati, Ohio) are mixed individually with one gram each of the perfumery substances of Table II of Example V, supra, until a homogeneous composition is obtained. The homogeneous composition is then treated under three atmospheres pressure at 180° C. for a period of three hours and the resulting liquid is placed into a soap mold. The resulting soap cakes, on cooling, manifest excellent aromas as set forth in Table II of Example V, supra.

EXAMPLE XI

PREPARATION OF A SOLID DETERGENT COMPOSITION

A detergent is prepared from the following ingredients according to Example II of Canadian Letters Patent 1,007,948 (the specification for which is incorporated by reference herein):

| Ingredients | Parts by Weight |
|---|---|
| "Neodol 45-11" ($C_{14}$–$C_{15}$ alcohol ethoxylated with 11 moles of ethylene oxide) | 12 |
| Sodium carbonate | 55 |
| Sodium citrate | 20 |
| Sodium sulfate, water | q.s. |

-continued

| Ingredients | Parts by Weight |
|---|---|
| brighteners | |

This detergent is a "phosphate-free" detergent. A total of 100 grams of this detergent is admixed separately with 0.15 grams of each of the perfume substances of Table II of Example V, supra. The detergent samples each have excellent aromas as set forth in table II of Example V, supra.

EXAMPLE XII

Utilizing the procedure of Example II at column 15 of U.S. Pat. No. 3,632,396 (the specification for which is incorporated by reference herein), a non-woven cloth substrate useful as a drier-added fabric softening article of manufacture is prepared, wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):
   57 percent $C_{20-22}$HAPS
   22 percent isopropyl alcohol
   20 percent antistatic agent
   1 percent of one of the perfume substances of Table II of Example V, supra.

A fabric softening composition prepared as set forth above having the above aroma characteristics as set forth in Table II of Example V, supra, essentially consists of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of substrate. The aroma set forth in Table II of Example V is imparted in a pleasant manner to the headspace in the dryer on operation thereof, using said dried-added fabric softening non-woven fabric.

What is claimed is:

1. At least one 2,2,3-trimethylcyclopentenyl acetone derivative defined according to a structure selected from the group consisting of:

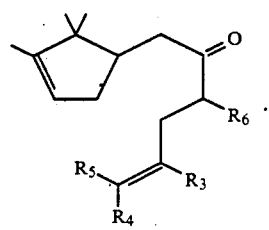

and

-continued

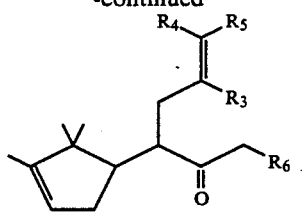

wherein $R_3$, $R_4$ and $R_5$ are the same or different hydrogen or methyl and $R_6$ is selected from the group consisting of hydrogen, methyl, ehtyl, propyl and isopropyl.

2. The compound having the structure:

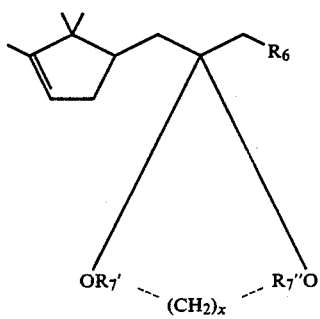

wherein $R_6$ is selected form the group consisting of hydrogen, methyl, ethyl, propyl and isopropyl and $R_7'$ and $R_7''$ are selected from the group consisting of methyl and ethyl or $R_7'$, $(CH_2)_x$ and $R_7''$ taken together represents ($C_2$-$C_6$ alkylene with x being 0, 1 or 2).

3. The composition defined according to claim 1 which is a mixture of compounds having the structures:

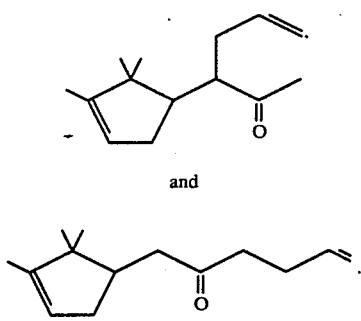

4. The compound of claim 2 having the structure:

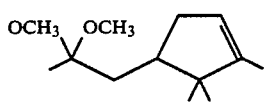

5. A process for augmenting or enhancing the aroma of perfume, cologne or perfumed article comprising the step of intimately admixing with said perfume, cologne or perfumed article an aroma augmenting or enhancing quantity of a 2,2,3-trimethylcyclopentenyl acetone derivative defined according to claim 1.

6. The process of claim 5 wherein the 2,2,3-trimethylcyclopentenyl acetone derivative is a mixture of compounds having the structures:

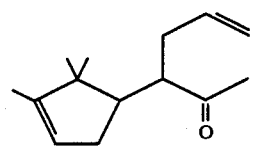

and

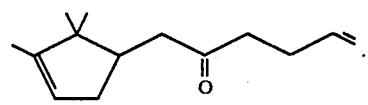

7. A process for augmenting or enhancing the aroma of a solid or liquid anionic, cationic, nonionic or zwitterionic detergent comprising the step of adding to said solid or liquid anionic, cationic, nonionic or zwitterionic detergent an aroma augmenting or enhancing quantity of at least one 2,2,3-trimethylcyclopentenyl acetone derivative defined according to claim 1.

8. The process of claim 7 wherein the 2,2,3-trimethylcyclopentenyl acetone derivative is a mixture of compounds having the structures:

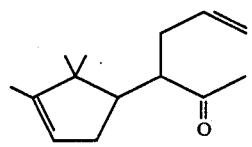

and

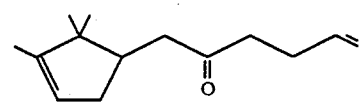

9. A perfume composition comprising a perfume base and intimately admixed therewith an aroma augmenting or enhancing quantity of at least one 2,2,3-trimethylcyclopentenyl acetone derivative defined according to claim 1.

10. A perfumed polymer comprising a polymer and intimately admixed therewith at least one 2,2,3-trimethylcyclopentenyl acetone derivative defined according to claim 1.

11. A fabric softener composition or fabric softener article comprising a fabric softener composition base or a fabric softener article base and intimately admixed therewith at least one 2,2,3-trimethylcyclopentenyl acetone derivative defined according to claim 1.

12. A cologne comprising alcohol, water and an aroma imparting quantity of at leas% one 2,2,3-trimethylcyclopentenyl acetone derivative defined according to claim 1.

* * * * *